(12) United States Patent
Li et al.

(10) Patent No.: US 11,058,852 B2
(45) Date of Patent: Jul. 13, 2021

(54) INTERVENTIONAL MEDICAL INSTRUMENT, DELIVERY APPARATUS, AND INTERVENTIONAL MEDICAL SYSTEM

(71) Applicant: Lifetech Scientific (Shenzhen) Co., Ltd., Shenzhen (CN)

(72) Inventors: Siyi Li, Shenzhen (CN); Anning Li, Shenzhen (CN)

(73) Assignee: Shenzhen Lifetech Respiration Scientific Co. Ltd., Shenzhen (CN)

( * ) Notice: Subject to any disclaimer, the term of this patent is extended or adjusted under 35 U.S.C. 154(b) by 194 days.

(21) Appl. No.: 16/066,249

(22) PCT Filed: Jun. 29, 2016

(86) PCT No.: PCT/CN2016/087768
§ 371 (c)(1),
(2) Date: Jun. 26, 2018

(87) PCT Pub. No.: WO2017/113667
PCT Pub. Date: Jul. 6, 2017

(65) Prior Publication Data
US 2019/0009057 A1    Jan. 10, 2019

(30) Foreign Application Priority Data
Dec. 31, 2015   (CN) .......................... 201511033393.7

(51) Int. Cl.
*A61M 25/01* (2006.01)
*A61F 2/966* (2013.01)
(Continued)

(52) U.S. Cl.
CPC .......... *A61M 25/0105* (2013.01); *A61B 1/05* (2013.01); *A61B 17/12022* (2013.01);
(Continued)

(58) Field of Classification Search
CPC .......... A61B 2017/12054; A61B 2017/00619; A61B 2017/00575; A61B 2017/00477;
(Continued)

(56) References Cited

U.S. PATENT DOCUMENTS

| 2002/0055767 A1* | 5/2002 | Forde ........................ A61F 2/01 623/1.11 |
| 2008/0139877 A1 | 6/2008 | Chu et al. |
| 2010/0152769 A1 | 6/2010 | Gesswein et al. |

FOREIGN PATENT DOCUMENTS

| CN | 101299975 A | 11/2008 |
| CN | 102395331 A | 3/2012 |

(Continued)

OTHER PUBLICATIONS

International Search Report dated Sep. 23, 2016 for corresponding PCT Application No. PCT/CN2016/087768.
(Continued)

*Primary Examiner* — Majid Jamialahmadi
(74) *Attorney, Agent, or Firm* — Raymond Sun (57) ABSTRACT

An interventional medical system (10) comprises an instrument (100) provided with a plug head (120) and a delivery cable (200) provided with a cable head (211), and further comprises a locking sleeve (300) movably sleeved onto the delivery cable (200). The cable head (211) comprises at least one resilient locking piece (123) extending approximately away from a central axis of the cable head (211). When under a radial restraint applied by the locking sleeve (300), the plug head (120) abuts the locking piece (123) such that the plug head (120) is connected to the cable head (211), and when the locking sleeve (300) has moved relative to the delivery cable (200) such that the locking piece (123) is no longer radially restrained, the locking piece (123) elastically moves away from the plug head (120) such that the instrument (100) is separated from the delivery cable (200).

7 Claims, 8 Drawing Sheets

(51) Int. Cl.
*A61B 17/12* (2006.01)
*A61B 17/00* (2006.01)
*A61F 2/01* (2006.01)
*A61B 1/05* (2006.01)
*A61F 2/95* (2013.01)

(52) U.S. Cl.
CPC .. *A61B 17/12104* (2013.01); *A61B 17/12122* (2013.01); *A61F 2/966* (2013.01); *A61B 2017/00477* (2013.01); *A61B 2017/00526* (2013.01); *A61B 2017/00862* (2013.01); *A61B 2017/1205* (2013.01); *A61B 2017/12054* (2013.01); *A61F 2/01* (2013.01); *A61F 2/011* (2020.05); *A61F 2002/9505* (2013.01); *A61F 2002/9665* (2013.01)

(58) Field of Classification Search
CPC ........... A61B 17/0057; A61B 17/12022; A61F 2002/9505; A61F 2002/9665; A61F 2/011; A61F 2/01; A61F 2/966
See application file for complete search history.

(56) References Cited

FOREIGN PATENT DOCUMENTS

| | | |
|---|---|---|
| CN | 103200984 A | 7/2013 |
| CN | 104254287 A | 12/2014 |
| CN | 105640620 A | 6/2016 |
| CN | 205458944 U | 8/2016 |
| WO | WO2007/055781 A1 | 5/2007 |
| WO | WO2013/148220 A1 | 10/2013 |

OTHER PUBLICATIONS

Office Action dated Aug. 28, 2017 for corresponding China Application No. 201511033393.7.
Office Action dated May 18, 2018 for corresponding China Application No. 201511033393.7.

\* cited by examiner

INTERVENTIONAL MEDICAL INSTRUMENT, DELIVERY APPARATUS, AND INTERVENTIONAL MEDICAL SYSTEM

TECHNICAL FIELD

The present disclosure relates to the field of interventional medical devices, and particularly relates to an interventional medical device placed at a selected part in a human body, a delivery apparatus for delivering the interventional medical device to the selected part, and an interventional medical system including the interventional medical device and the delivery apparatus.

BACKGROUND ART

An interventional therapy is a method for treating a disease in a non-invasive way of delivering a material, a medical device and a medicine to a to-be-treated part via a catheter under the guide of a certain medical imaging equipment. At the present time, interventional therapy has become one of three major modern medical treatment methods, which also include traditional medical treatment and surgical treatment, and is most widely applied to heart and vascular diseases.

Compared with a traditional medical treatment, an interventional therapy achieves clinical effects which may not be achieved by conventional drug therapies, and has a trend of replacing surgical treatment in some cases. For example, radiofrequency ablation treats paroxysmal supraventricular tachycardia, atrial fibrillation, atrial flutter, various premature beats and ventricular tachycardia; an occluder device treats congenital heart disease, patent ductus arteriosus and a hole-II central atrial septal defect; balloon dilatation treats diseases such as mitral stenosis and pulmonary valve stenosis; stent implantation treats coronary heart diseases, various types of vascular stenosis and the like; a pacemaker treats bradycardia, congestive heart failures and the like and prevents sudden death; and some diseases may be completely eradicated. The above-mentioned diseases are not only treated by traditional medicines and surgical operation. Compared with the surgical operation, the interventional therapy has outstanding advantages as follows: (1) a small wound and less pain: by virtue of being non-invasive, this operation is completed only through a catheter with a thickness of 2 to 3 mm, so that the wound is small; (2) quick recovery: because of the small wound, a patient recovers quickly after an operation; generally, a patient subjected to the interventional therapy for a cardiovascular disease can do stretches off a bed in 24 hours after an operation, and can take care of him/herself in his/her daily lives; (3) good treatment effect and safe operation: being non-invasive, general anesthesia and wound healing are needed after an interventional therapy, many complications which are often caused in and after the surgical treatment are avoided, and the safety is greatly improved; and (4) in accordance with a desire for beauty by modern people: by virtue of being non-invasive, no wounds and scars are left after a treatment, so that no treatment traces are seen from the surface after an interventional therapy, and this advantage is particularly suitable for children, women and practitioners in industries having relatively high requirements for appearances.

It can be seen that the application of a percutaneous intervention therapy for disease treatment is becoming more and more extensive. Generally, many kinds of materials, devices and medicines may be placed in the heart and arteriovenous vessels of a human body through a catheter interventional therapy. For example, a valve repair device, a heart defect occluder, a vascular plug, a vascular filter, a lung volume reduction device and the like can be placed at selected positions through the interventional therapy.

At present, an interventional medical device and a delivery cable are generally utilized in threaded connection in an interventional therapy. Threads may be classified into left-hand threads and right-hand threads according to their rotational forwarding directions. When the interventional medical device and the delivery cable include the right-hand threads, the delivery cable is clockwise rotated to enable the interventional medical device to be connected with the delivery cable; and to relieve the connection between the interventional medical device and the delivery cable by anticlockwise rotation. However, due to the complexity of body anatomical structures such as the heart, an arteriovenous vascular system and a bronchial system, interactions such as push-and-pull, bending and torsion between the interventional medical device and the delivery cable may be caused in a process of pushing the interventional medical device to a selected region of the human body. In case of anticlockwise torsion, meshing portions of a threaded connection region between the interventional medical device and the delivery cable decreases, so that there is a risk that the interventional medical device would fall off before reaching the selected region in a human body; and in case of clockwise torsion, the meshing portions of the threaded connection region between the interventional medical device and the delivery cable increases, and even as the meshing is too tight, a friction force between internal and external threads exceeds a certain threshold value, which leads to difficulty in separation of the interventional medical device from the delivery cable during the subsequent release process, and results in surgical failure. The above two cases may cause harm to the patient and increase the risks of surgery.

SUMMARY OF THE INVENTION

Based on the above-mentioned problem, it is necessary to provide an interventional medical system for an interventional therapy, an interventional medical device and an interventional medical device delivery apparatus to solve the problem in connection between a medical device and the end portion of a delivery cable in the prior art.

The present disclosure provides an interventional medical system, including a device provided with a plug head portion and a delivery cable provided with a cable head portion. The interventional medical system further includes a locking sleeve movably surrounding the outside of the delivery cable. The cable head portion includes at least one elastic locking piece which extends approximately away from the central axial line of the cable head portion. Under radial restriction applied by the locking sleeve, the plug head portion abuts the locking piece such that the plug head portion is connected with the cable head portion, and when the locking sleeve moves relative to the delivery cable to a position where the locking piece is no longer radially restrained, the locking piece elastically moves away from the plug head portion such that the device is separated from the delivery cable.

In one embodiment, the cable head portion includes multiple locking pieces; the multiple locking pieces of the cable head portion form a limiting slot in an encircling manner; under radial restriction applied by the locking sleeve, the plug head portion is contained in the limiting slot, so that the plug head portion is connected with the cable head portion.

In one embodiment, at least one locking slot is formed in the side wall of the plug head portion; and when the plug head portion is connected with the cable head portion, at least one locking piece of the cable head portion is at least contained in the locking slot of the plug head portion.

In one embodiment, the locking slot of the plug head portion extends along an axial direction of the plug head portion, and penetrates through the proximal end surface of the plug head portion.

The present disclosure provides an interventional medical system, including a device provided with a plug head portion and a delivery cable provided with a cable head portion. The interventional medical system further includes a locking sleeve movably surrounding the outside of the delivery cable. The plug head portion includes at least one locking slot which penetrates through the proximal end surface of the plug head portion. The cable head portion includes at least one elastic locking piece which extends approximately away from the central axial line of the cable head portion. Under radial restriction applied by the locking sleeve, at least one locking piece of the cable head portion is contained in each locking slot of the plug head portion such that the plug head portion is connected with the cable head portion, and when the locking sleeve moves relative to the delivery cable to a position where the locking pieces of the cable head portion are no longer radially restrained, the locking pieces of the cable head portion elastically move away from the locking slots of the plug head portion such that the device is separated from the delivery cable.

In one embodiment, the plug head portion includes multiple mutually separated locking pieces; each locking slot of the plug head portion is positioned between two adjacent locking pieces of the plug head portion; and under radial restriction applied by the locking sleeve, each locking piece of the cable head portion is contained in one locking slot of the plug head portion such that the plug head portion is connected with the cable head portion.

In one embodiment, the length of the proximal end of each locking slot of the plug head portion in a circumferential direction of the plug head portion is less than that of the distal end of the locking slot of the plug head portion in the circumferential direction of the plug head portion.

In one embodiment, the locking slot of the plug head portion includes a T-shaped structure having a distal end, and the length of the distal end of the T-shaped structure in the circumferential direction of the plug head portion is the maximum length of the T-shaped structure in the circumferential direction of the plug head portion.

In one embodiment, the interventional medical system further includes a limiting part contained in the delivery cable; and when the plug head portion is connected with the cable head portion, the locking pieces of the cable head portion are also clamped between the limiting part and the locking sleeve.

In one embodiment, the delivery cable includes a hollow cable section; the locking pieces of the cable head portion are arranged at the distal end of the cable section; and a unilateral gap between the delivery cable and the limiting part is less than the wall thickness of the cable section.

In one embodiment, the thicknesses of the locking pieces of the cable head portion are uniform.

In one embodiment, each locking slot has a proximal end and an distal end, and the length of the proximal end of each locking slot of the plug head portion in the circumferential direction of the plug head portion is less than that of the distal end of the locking slot of the plug head portion in the circumferential direction of the plug head portion, and the length of the proximal end of each locking piece of the plug head portion along the circumferential direction of the plug head portion is greater than that of the distal end of the locking piece of the plug head portion along the circumferential direction of the plug head portion.

In one embodiment, the plug head portion includes a hollow main body section having a proximal end surface, and the locking pieces of the plug head portion are arranged on the proximal end surface of the hollow main body section.

In one embodiment, the main body section and the locking pieces of the plug head portion are of an integrated structure formed by cutting one hollow tube.

In one embodiment, the outer surfaces of the locking pieces of the plug head portion are curved surfaces, and the outer diameter of a whole formed by the locking pieces of the plug head portion is greater than that of the main body section; part of the end surface of the distal end of the locking sleeve is sunken towards the proximal end of the locking sleeve to form at least one containing groove; and when the locking sleeve radially restrains the locking pieces of the cable head portion, the locking pieces of the plug head portion are at least partially contained in the containing grooves.

The present disclosure provides an interventional medical device, including a plug head portion positioned at the proximal end of the interventional medical device; and at least one locking slot is formed in the side wall of the plug head portion.

In one embodiment, the locking slots of the plug head portion extend along an axial direction of the plug head portion, and penetrate through the proximal end surface of the plug head portion.

The present disclosure provides an interventional medical device, including a plug head portion positioned at the proximal end of the interventional medical device; and the plug head portion includes at least one locking slot which penetrates through the proximal end surface of the plug head portion.

In one embodiment, each locking slot has a proximal end and a distal end, and the length of the proximal end of each locking slot along a circumferential direction of the plug head portion is less than that of the distal end of the locking slot along the circumferential direction of the plug head portion.

In one embodiment, each locking slot includes a T-shaped structure having a distal end; and the length of the distal end of the T-shaped structure in the circumferential direction of the plug head portion is the maximum length of the T-shaped structure in the circumferential direction of the plug head portion.

In one embodiment, the locking piece is a T-shaped piece and has a proximal end, and the length of the proximal end of the locking piece along the circumferential direction of the plug head portion is the maximum length of the locking piece along the circumferential direction of the plug head portion.

In one embodiment, the plug head portion includes a hollow main body section having a proximal surface; the plug head portion includes multiple mutually separated locking pieces; each locking slot of the plug head portion is positioned between two adjacent locking pieces of the plug head portion; and the locking pieces of the plug head portion are arranged on the proximal end surface of the hollow main body section.

In one embodiment, the main body section and the locking pieces are of an integrated structure formed by cutting one hollow tube.

In one embodiment, the outer surfaces of the locking pieces are curved surfaces, and the outer diameter of a whole formed by the locking pieces of the plug head portion is greater than that of the main body section.

The present disclosure provides a delivery apparatus of an interventional medical device, including a delivery cable. The delivery cable includes a cable head portion detachably connected with the interventional medical device. The delivery apparatus further includes a locking sleeve movably surrounding the outside of the delivery cable. The cable head portion includes at least one elastic locking piece which extends approximately away from the central axial line of the cable head portion. The locking piece is compressed under radial restriction applied by the locking sleeve, and restores when the locking sleeve moves relative to the delivery cable to a position where the locking piece is no longer radially restrained.

In one embodiment, the cable head portion includes multiple mutually separated locking pieces.

In one embodiment, each locking piece is a T-shaped piece and has a distal end, and the length of the distal end of each locking piece along a circumferential direction of the cable head portion is the maximum length of the locking piece along the circumferential direction of the cable head portion.

In one embodiment, the thicknesses of the locking pieces are uniform.

In one embodiment, the delivery apparatus further includes a limiting part contained in the delivery cable, and the limiting part cooperates with the locking sleeve to clamp the locking pieces between the limiting part and the locking sleeve.

In one embodiment, the delivery cable includes a hollow cable section having a distal end; the locking pieces are arranged at the distal end of the cable section; and a unilateral gap between the delivery cable and the limiting part is less than the wall thickness of the cable section.

Compared with the prior art, the present disclosure has the following advantages: the interventional medical system of the present disclosure achieves a connection between the interventional medical device and the delivery cable through the use of locking pieces, thereby completely avoiding connecting a threaded connection of the interventional medical device with the delivery cable, guaranteeing a normal release of the interventional medical device, and reducing the surgery risk.

DETAILED DESCRIPTION OF THE INVENTION

For the purpose of making the objectives, features and advantages of the present disclosure clearer, a detailed description to specific implementation modes of the present disclosure will be made below together with corresponding drawings. Many specific details are described in the following descriptions to facilitate a full understanding of the present disclosure. But the present disclosure may be implemented in many other ways different from those described herein. Persons skilled in the art can make similar improvements without departing from the scope of the present disclosure, so that the present disclosure will not be limited by specific embodiments disclosed below.

It should be noted that when one element is being "fixed" on another element, it may be directly on another element or an intermediate element also may exist. When one element is deemed as being "connected to" another element, it may be directly connected to another element or an intermediate element may exist at the same time. In the interventional field, generally, the end close to an operator is a proximal end, and the end far away from the operator is a distal end.

It also should be noted that an interventional medical device in this implementation mode includes a medical device main body portion and a plug head portion connected with the medical device main body portion. The medical device main body portion is a portion of the interventional medical device, which is used for a medical procedure, and the plug head portion is a portion of the interventional medical device, which is connected with a delivery cable.

Unless otherwise specified, all technical and scientific terms used herein are the same as meanings of general understandings of technical persons skilled in the art of the present disclosure. The terms used in the description of the present disclosure in this text are only to describe specific embodiments, but not intended to limit the present disclosure. The terms "and/or" used in this text include any and all combinations of one or multiple relevant listed items.

Figure 1:
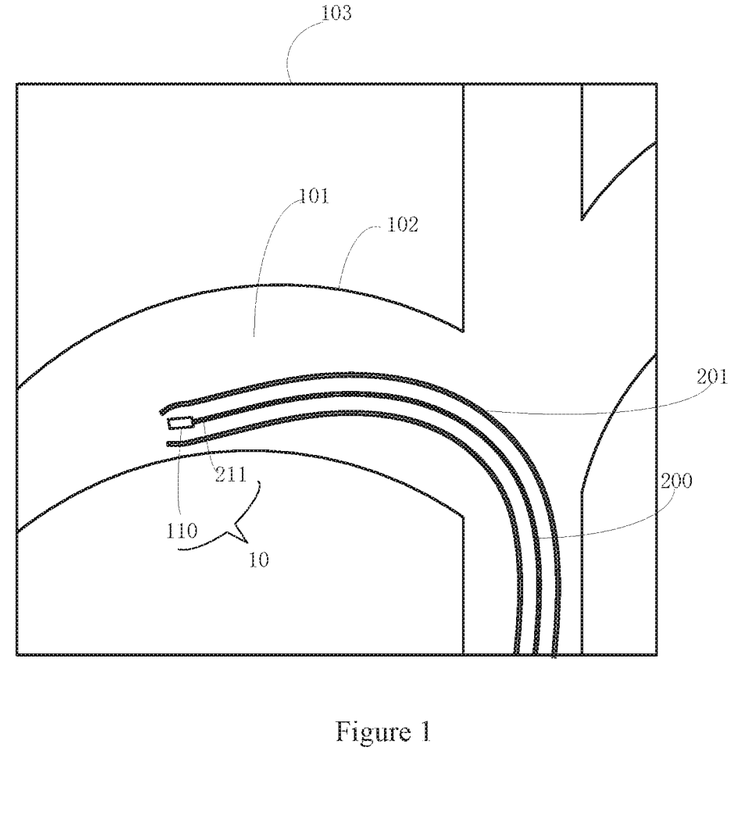
FIG. 1 is a schematic diagram of showing the use of one embodiment of the present disclosure in the human body.

An implementation mode of the present disclosure is applied to interventional medical equipment. As shown in FIG. 1, this medical equipment includes an interventional medical system 10. The interventional medical system 10 includes an interventional medical device 110, and a delivery cable 200 for delivering the interventional medical device 110. Generally, after being connected with the distal end 210 of the delivery cable 200, the interventional medical device 110 is placed in a catheter 201, and is delivered in a tissue cavity 101 of a patient, and then a connection between the delivery cable 200 and the interventional medical device 110 is cut off when the interventional medical device 110 moves to a selected position, so that the interventional medical device 110 is placed at the selected position to implement the interventional therapy. The tissue cavity 101 may be a cavity formed by a tissue wall 102. For example, the tissue cavity 101 includes a blood vessel cavity, an enteric cavity, a heart chamber and a trachea. Of course, the tissue cavity 101 may also include internal tissue cavities in the human body where the device may arrive at during the interventional therapy at the present time, and any one of internal tissue cavities in the human body where the device will arrive at during the interventional therapy in the future. The interventional medical device 110 mentioned in this text may be any one medical device for the interventional therapy, such as a heart defect occluder, a valve repair device, a vascular plug, a vascular filter and a lung volume reduction device. The delivery cable 200 is a long and thin object for the interventional treatment, such as a steel cable and a catheter, and its distal end is connected with the interventional medical device 110. The distal end herein is the end farthest from the operator in FIG. 1, and the relatively proximal end is the end closest to the operator.

Of course, to enable medical staff to clearly know whether the interventional medical device 110 is delivered to the selected position or not, the medical equipment further may also include a camera apparatus, a monitor and the like. The camera apparatus is placed in the catheter 201, and shoots video data of the tissue cavity 101 along with the distal end of the catheter 201; and then the video data are transmitted to the monitor to display corresponding images on an interface 103, thereby providing precise positioning data of the interventional therapy for the medical staff.

To avoid the difficulties in releasing the interventional medical device 110 at the correct selected position so that a medical risk factor increases due to the problem in connection between the interventional medical device 110 and the delivery cable 200, in the embodiments of the present disclosure, an improvement is made to an interventional medical system 10. The specific improvement is described below together with the drawings.

One embodiment of the present disclosure provides an interventional medical system 10 for interventional therapy.

Figure 2:
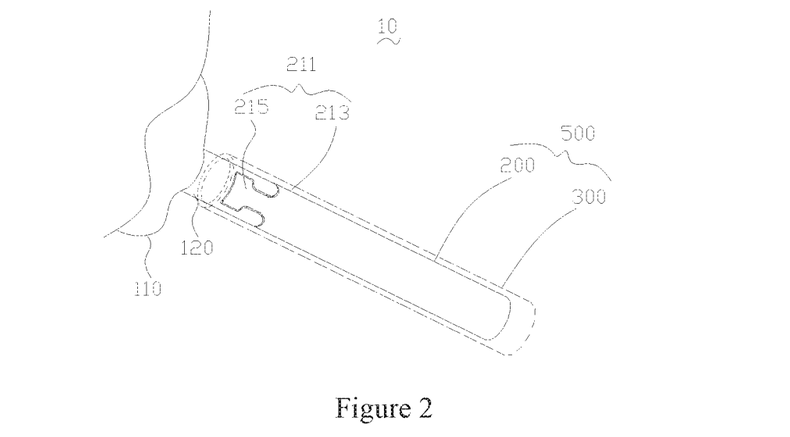
FIG. 2 is a schematic diagram of the structure of an interventional medical system according to one embodiment of the present disclosure.

With reference also to FIG. 2, the interventional medical system 10 includes an interventional medical device 110 and a delivery apparatus 500. The device 110 includes a plug head portion 120 positioned on the interventional medical device 110. The delivery apparatus 500 includes a delivery cable 200 and a locking sleeve 300 which surrounds the delivery cable 200 and may move relative to an axial direction of the delivery cable 200. The delivery cable 200 includes a cable head portion 211 which may be radially compressed and may expand to a natural state by itself after an external force is withdrawn.

Figure 3:
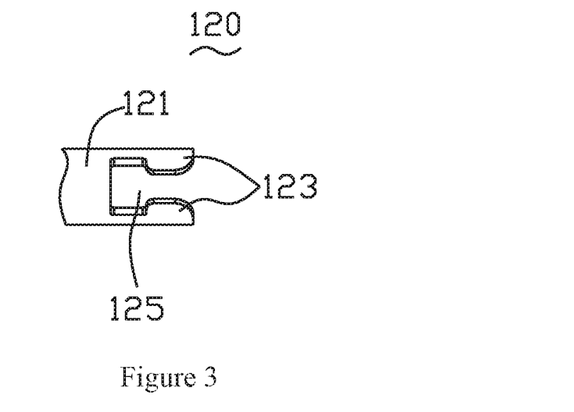
FIG. 3 is a schematic diagram of the structure of a plug head portion of an interventional medical device of the interventional medical system in FIG. 2.
Figure 4:
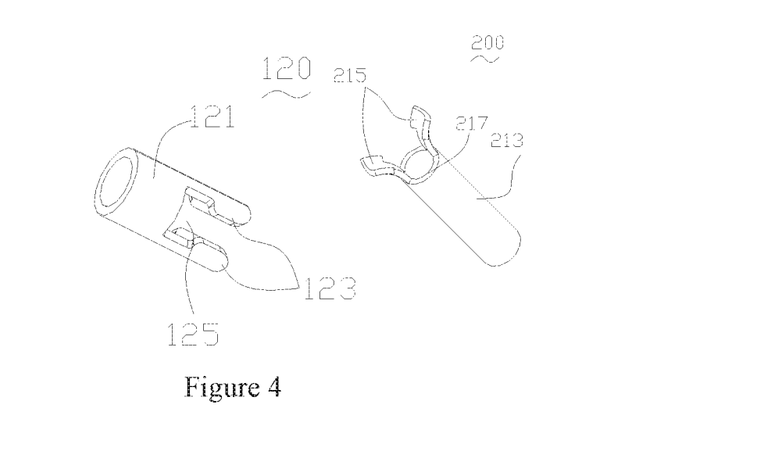
FIG. 4 is a schematic diagram from another view of the plug head portion of the interventional medical device of the interventional medical system in FIG. 2.

With reference also to FIG. 3 and FIG. 4, the plug head portion 120 includes a hollow main body section 121 and at least two first locking pieces 123 distributed along a circumferential direction of the main body section 121 in a spaced-apart manner. A first locking slot 125 is formed between two adjacent first locking pieces 123 in the circumferential direction of the plug head portion 120. Each first locking slot 125 extends through the proximal end surface of the plug head portion 120, and the length of the proximal end of the first locking slot 125 in the circumferential direction of the plug head portion 120 is less than that of the distal end of the first locking slot 125 in the circumferential direction of the plug head portion 120.

In this embodiment, there are two first locking pieces 123, and the two first locking pieces 123 are arranged on the proximal end surface of the main body section 121; each first locking piece 123 is a T-shaped piece, and the length of its distal end along the circumferential direction of the plug head portion 120 is the maximum length of the first locking piece 123 along the circumferential direction of the plug head portion 120. Therefore, in the circumferential direction of the plug head portion 120, two T-shaped first locking slots 125 are formed between two first locking pieces 123. Preferably, in this embodiment, the main body section 121 and the two first locking pieces 123 are of an integrated structure formed by cutting one hollow nickel-titanium tube. It can be understood that the main body section 121 and the two locking pieces 123 also may be made of common metal materials for interventional medical devices, such as stainless steel or a cobalt-chromium alloy. It also can be understood that the two first locking pieces 123 also may achieve the same effect by adopting other machining modes, such as linear cutting, powder metallurgy and casting. It can be understood that the first locking slots 125 also may be L-shaped, C-shaped or in other shapes, and its shape may be designed as required.

Figure 5:
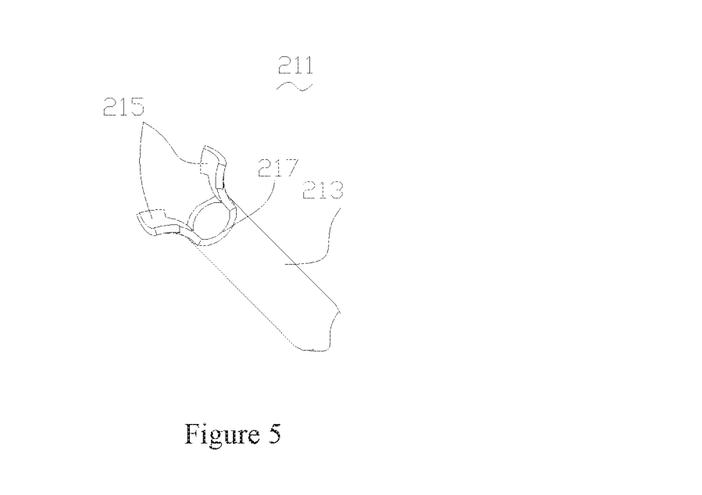
FIG. 5 is a schematic diagram of the structure of a cable portion of a delivery cable of the interventional medical device in FIG. 2.

With reference also to FIG. 5, the cable head portion 211 of the delivery cable 200 includes a hollow cable section 213 and at least two elastic second locking pieces 215 distributed along the circumferential direction of the cable section 213 in a spaced-apart manner. The at least two second locking pieces 215 may convert between a compressed state and an expanded state, in other words, each second locking piece 215 may be radially shrunk (namely in the compressed state) under the action of an external force; and after the external force is withdrawn, each second locking piece 215 may be restored to a natural state (namely the expanded state). The thickness of each second locking piece 215 is uniform and consistent, and each second locking piece 215 extends approximately away from the central axial line of the cable head portion 211. In this present disclosure, the situation that each second locking piece 215 extends approximately away from the central axial line of the cable head portion 211 means that when each second locking piece 215 extends approximately away from the central axial line of the cable head portion 211, some portions of each second locking piece 215 are allowed to get close to the central axial line of the cable head portion 211 compared with their adjacent portions; and under radial restriction applied by the locking sleeve 300, each second locking piece 215 may be at least partially contained in each first locking slot 125 to integrally connect the interventional medical device 110 with the delivery cable 200.

When the at least two second locking pieces 215 are in a compressed state, one second locking slot 217 is formed between two adjacent second locking pieces 215 in the circumferential direction of the cable head portion 211. Each second locking slot 217 penetrates through the distal end surface of the cable head portion 211.

In this embodiment, there are two second locking pieces 215, and the two second locking pieces 215 are arranged on the distal end surface of the cable section 213; each second locking piece 215 is a T-shaped piece, and the length of its distal end along the circumferential direction of the cable portion 211 is the maximum length of the second locking piece 215 along the circumferential direction of the cable section 211. Therefore, when the two second locking pieces 215 are in a compressed state, in the circumferential direction of the cable section 211, two T-shaped second locking slots 217 are formed between the two second locking pieces 215. Preferably, in this embodiment, the cable section 213 and the two second locking pieces 215 are of an integrated structure formed by cutting one hollow nickel-titanium tube and then carrying out thermal shaping on the cut tube; when the two second locking pieces 215 are in a compressed state, the outer diameter of a whole formed by the two second locking pieces 215 is equal to that of the cable section 213. It can be understood that the second locking pieces 215 and the cable section 213 also may be separately and independently formed, and then are connected into a whole in a connection by way of welding, adhesion, screwing and the like. It also can be understood that the second locking pieces 215 also may be made of other metal materials with relatively good elasticity, such as a cobalt-chromium alloy.

It can be understood that the first locking slots also may be in other shapes such as a cross shape and an I shape, and then the length of the proximal end of each first locking slot in the circumferential direction of the plug head portion is greater than or equal to that of the distal end of a first locking slot in the circumferential direction of the plug head portion; each second locking piece which matches with each first locking slot in shape may still be contained in one corresponding first locking slot under the radial restriction applied by the locking sleeve to connect the plug head portion with the cable head portion.

Figure 6:
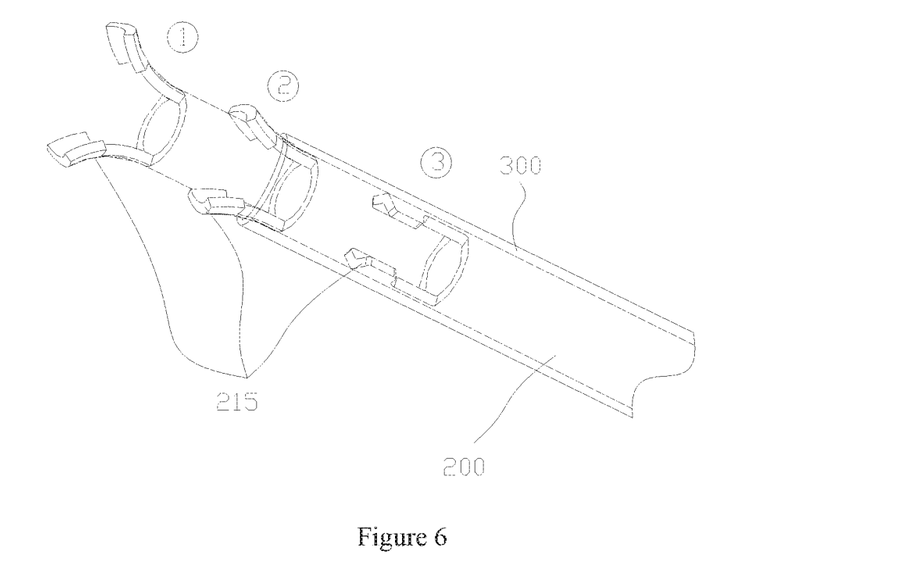
FIG. 6 is a schematic diagram of a state of the delivery cable of the interventional medical system in FIG. 2 gradually entering a locking sleeve.
Figure 7:
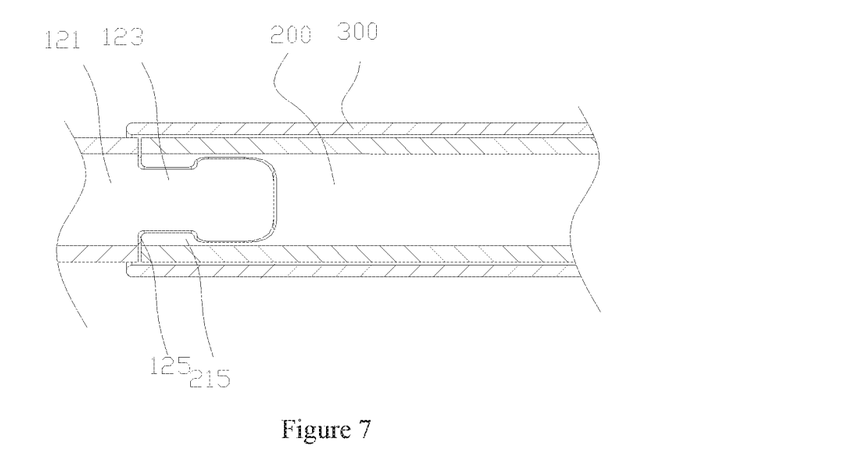
FIG. 7 is a schematic diagram of a locking state of the interventional medical system in FIG. 2.

With reference also to FIG. 6, the locking sleeve 300 is a hollow tubular body, which surrounds the outside of the delivery cable 200 and may move relative to the axial direction of the delivery cable 200. When moving relative to the axial direction of the locking sleeve 300, the two second locking pieces 215 of the delivery cable 200 are radially restrained by the locking sleeve 300, and may be limited from an expanded state (a state 1 as shown in FIG. 6) into a cylindrical state (namely the compressed state which is a state 3 as shown in FIG. 6). In this embodiment, the inner diameter of the locking sleeve 300 is slightly greater than the outer diameter of the cable section 213 to ensure that the two locking pieces 215 may be clamped into the first locking slots 125 after being completely compressed.

Figure 8:
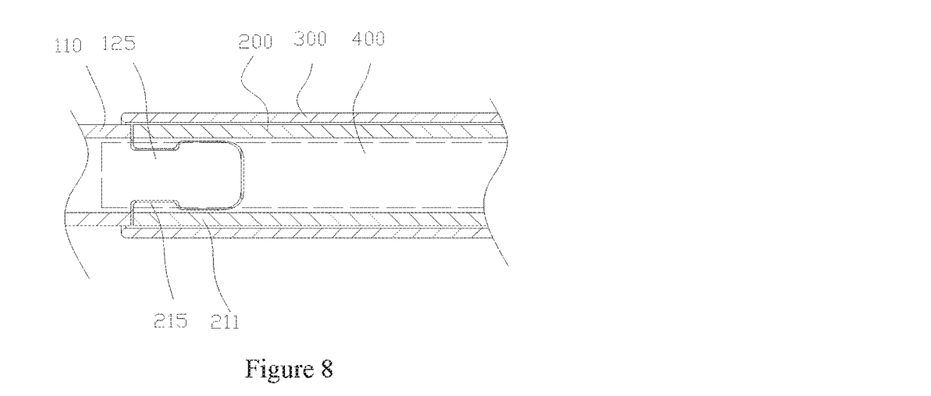
FIG. 8 is a schematic diagram of part of a profile of the interventional medical system in FIG. 2 after a limiting part is added in the interventional medical system.

With reference to FIG. 8, the delivery apparatus 500 of the interventional medical system 10 also includes a cylindrical limiting part 400. The limiting part 400 is contained in the delivery cable 200, and is used for supporting the second locking pieces 215. When the interventional medical system 10 is in a locked state, the distal end of the limiting part 400 extends through the distal end of the cable portion 211, and cooperates with the locking sleeve 300 to clamp the second locking pieces 215 between the outer wall of the limiting part 400 and the inner wall of the locking sleeve 300 to prevent looseness between the device 110 and the delivery cable 200, which is caused by misalignment between the second locking pieces 215 and the first locking slots 125 due to a rare circumstance that the second locking pieces 215 deform too much towards a direction close to the longitudinal central axis of the cable portion 211. Preferably, in this embodiment, a unilateral gap between the delivery cable 200 and the limiting part 400 is less than the wall thickness of the cable section 213, and the limiting part 400 may move relative to the delivery cable 200. In other implementation modes of the present disclosure, the limiting part 400 may be omitted. In other implementation modes of the present disclosure, the limiting part 400 also may be fixed with the delivery cable 200 to form a whole.

Figure 9:
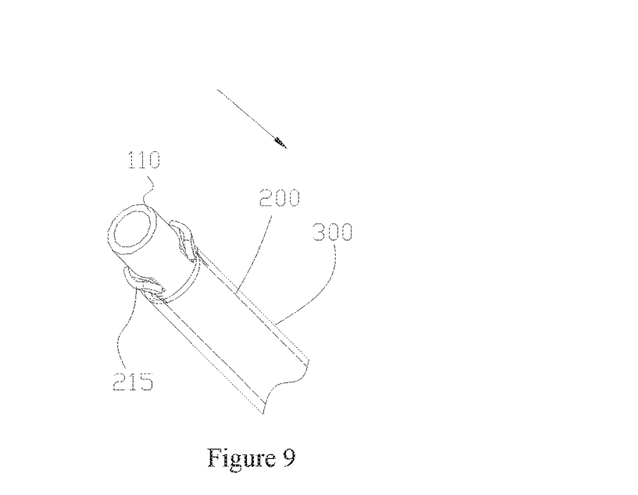
FIG. 9 is a schematic diagram of the interventional medical system in FIG. 2 after a connection between the interventional medical device and the delivery cable in the interventional medical system is partially released.
Figure 10:
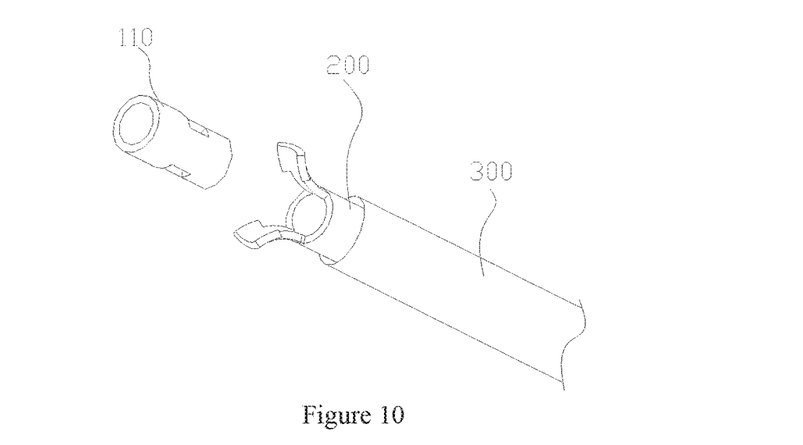
FIG. 10 is a schematic diagram of the interventional medical system in FIG. 2 after the connection between the interventional medical device and the delivery cable in the interventional medical system is completely released.
Figure 11:
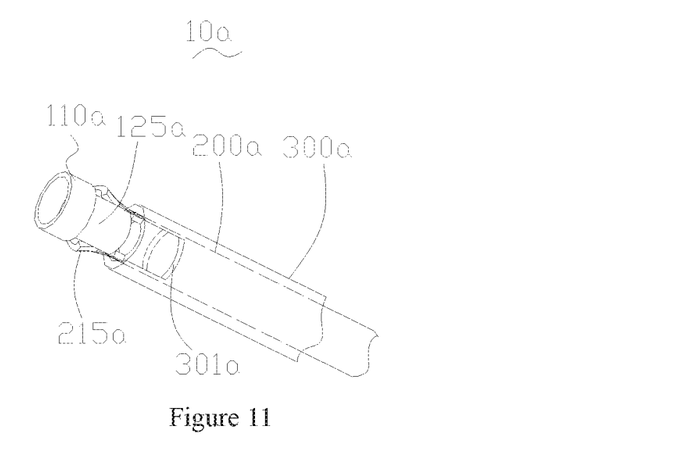
FIG. 11 is a schematic diagram of an interventional medical system provided by another embodiment of the present disclosure.

With reference together to FIG. 8, FIG. 10 and FIG. 11, when the interventional medical system 10 is in a locked state, namely when the plug head portion 120 is connected with the cable head portion 211, the two second locking pieces 215 are radially restrained by the locking sleeve 300 such that they are limited from an expanded state into a cylindrical state (namely a compressed state), and are clamped into the first locking slots 125. As the length of the distal end of each second locking piece 215 along the circumferential direction of the cable head portion 211 is greater than that of the proximal end of the second locking piece 215 along the circumferential direction of the cable head portion 211, connection is formed between the device 110 and the delivery cable 200, wherein the device 110 and the delivery cable 200 may not relatively move in both the axial direction and the circumferential direction; when the locking sleeve 300 moves relative to the delivery cable 200 towards a direction away from the device 110 until the second locking pieces 215 elastically move away from the first locking slots 125, the device 110 is separated from the delivery cable 200. Therefore, a releasing process of the device 110 is as follows: in a locked state, the delivery cable 200 is stationary, and the locking sleeve 300 is moved along an arrow direction (namely the direction away from the device 110) as shown in FIG. 9; the second locking pieces 215 having elasticity are gradually withdrawn from the restriction of the locking sleeve 300 to restore preset horn shapes such that the second locking pieces 215 elastically move away from the first locking slots 125 gradually; and when the second locking pieces 215 have completely and elastically moved away from the first locking slots 125, the device 110 is separated from the delivery cable 200 (as shown in FIG. 10), thus fulfilling the objective of releasing the device 110.

According to the interventional medical device 100 of this embodiment, when the plug head portion 120 is connected with the cable head portion 211, one second locking piece 215 is clamped into one first locking slot 125 under the radial restriction applied by the locking sleeve 300; and when the locking sleeve 300 moves relative to the delivery cable 200 towards the direction away from the device 110 until the second locking pieces 215 elastically move away from the first locking slots 125, the device 110 is separated from the delivery cable 200, thereby completely avoiding a threaded connection for the device 110 and the delivery cable, guaranteeing normal release of the device 110, and reducing the medical risk. In addition, during the releasing process, it only necessary for the locking sleeve 300 to move relative to the delivery cable 200 towards the direction away from the device 110 until the second locking pieces 215 elastically move away from the first locking slots 125; and the operation process is relatively simple, thus shortening the surgery time and reducing the surgery risk for a patient.

It can be understood that in other embodiments there may be one second locking piece 215 or one first locking slot 125 as long as the second locking piece 215 may be at least partially contained in the first locking slot 125 under the radial restriction applied by the locking sleeve 300 to connect the interventional medical device 110 with the delivery cable 200. It also may be understood that in other embodiments, under the radial restriction applied by the locking sleeve 300, each first locking slot 125 also may contain two or more second locking pieces 215 as long as the interventional medical device 110 is connected with the delivery cable 200. For example, two or more second locking pieces 215 abut the slot wall of one first locking slot 125 or are clamped in one first locking slot 125.

With reference to FIG. 11, an interventional medical system 10a provided by another embodiment of the present disclosure is approximately the same as the interventional medical system 10, and includes an interventional medical device 110a, a delivery cable 200a, and a locking sleeve 300a which surrounds the delivery cable 200a and may move relative to an axial direction of the delivery cable 200a.

Figure 12:
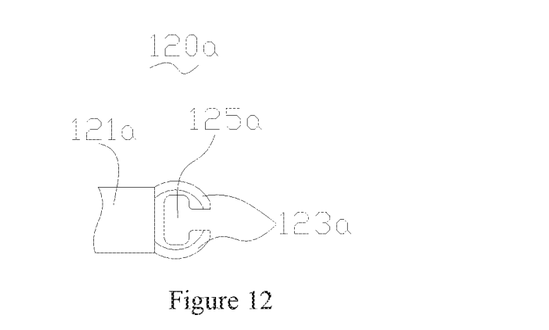
FIG. 12 is a schematic diagram of a plug head portion of an interventional medical device of the interventional medical system in FIG. 11.
Figure 13:
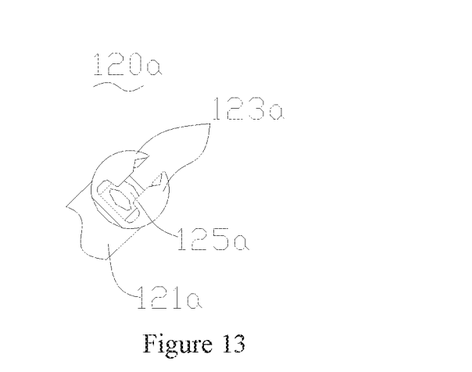
FIG. 13 is a schematic diagram from another view of the plug head portion of the interventional medical device of the interventional medical system in FIG. 11.

With reference to FIG. 12 and FIG. 13, a plug head portion 120a of the device 110a is approximately the same as the plug head portion 120, and also includes a hollow main body section 121a and at least two first locking pieces 123a distributed along a circumferential direction of the main body section 121a in a spaced-apart manner; and in the circumferential direction of the plug head portion 120a, one first locking slot 125a is formed between two adjacent first locking pieces 123a, but the difference is that the outer surfaces of the first locking pieces 123a are curved surfaces, and the outer diameter formed by all of the at least two first locking pieces 123a is greater than that of the main body section 121a to prevent the proximal end of the device 110a from scratching a human body tissue during the process of implanting the device 110a into a human body. In this embodiment, the main body section 121a and the first locking pieces 123a are independently formed, and then are fixedly connected by welding. It can be understood that the main body section 121a and the first locking pieces 123a also may be fixedly connected through other connection methods such as adhesion and screwing. Preferably, the plug head portion 120a may be integrated; for example, the plug head portion 120a is made in one piece by adopting turning, milling, drilling, grinding and other machining modes; and for another example, the plug head portion 120a may be formed by adopting other forming modes (such as powder metallurgy and casting).

The delivery cable 200a is the same as the delivery cable 200, so no additional details will be described here.

Figure 14:
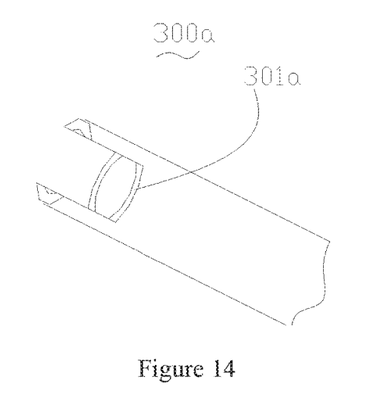
FIG. 14 is a schematic diagram of a locking sleeve of the interventional medical system in FIG. 11.

With reference also to FIG. 14, the locking sleeve 300a is approximately the same as the locking sleeve 300, but the difference is that part of the end surface of the distal end of the locking sleeve 300a is sunken towards the proximal end of the locking sleeve 300a to form at least two U-shaped containing grooves 301a distributed in a spaced-apart manner. The containing grooves 301a are used for containing the first locking pieces 123a when the locking sleeve 300a restrains the second locking pieces of the delivery cable 200a, thereby reducing the outer diameter of the locking sleeve 300a.

Figure 15:
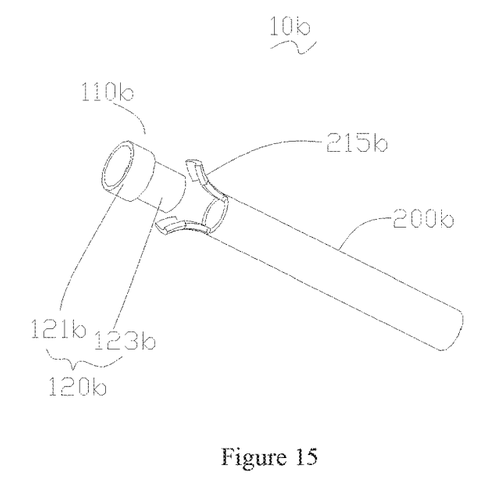
FIG. 15 is a schematic diagram of an interventional medical system provided by another embodiment of the present disclosure.

With reference to FIG. 15, an interventional medical system 10b provided by another embodiment of the present disclosure is approximately the same as the interventional medical system 10, and includes an interventional medical device 110b, a delivery cable 200b, and a locking sleeve (not shown in the figure) which surrounds the delivery cable and may move relative to an axial direction of the delivery cable 200b.

A plug head portion 120b of the device 110b includes a main body section 121b and a connection section 123b connected with the main body section 121b. In this embodiment, the main body section 121b and the connection section 123b are both hollow columnar bodies. It can be understood that in other embodiments, the connection section 123b also may be a solid columnar body.

The structure of the delivery cable 200b is approximately the same as that of the delivery cable 200, but the difference is that the inner surfaces of second locking pieces 215b of the delivery cable 200b are roughened to increase the friction force between the connection section 123b and the second locking pieces 215b.

The locking sleeve is approximately the same as the locking sleeve 300, but the difference is that the thickness and the size of the locking sleeve 300b may be different from those of the locking sleeve 300 based on the clinical requirements, and no additional details will be described here.

When the locking sleeve radially restrains the second locking pieces 215b of the delivery cable 200b to the side wall of the connection section 123b of the plug head portion 120b (namely when the second locking pieces 215b form a limiting slot for containing the connection section 123b in an encircling manner under radial restriction applied by the locking sleeve), a radial pressure is caused between the second locking pieces 215b and the side wall of the connection section 123b, so that a friction force for preventing relative movement between the delivery cable 200b and the device 110b is generated between the second locking pieces 215b and the connection section 123b, and the connection between the delivery cable 200b and the device 110b will be achieved.

It can be understood that the side wall of the connection section 123b may also be roughened to enhance the friction force between the second locking pieces 215b and the connection section 123b. It also can be understood that friction force enhancing pieces, such as rubber and sponge, for increasing the friction force, may also be arranged on the connection section 123b and/or the second locking pieces 215b.

It can be understood that in other embodiments, there may be one second locking piece 215b as long as under the radial restriction applied by the locking sleeve, the inner surface, which is close to the longitudinal central axis of the delivery cable 200b, of the second locking piece 215b may abut the side wall of the connection section 123b to connect the interventional medical device 110b with the delivery cable 200b.

Figure 16:
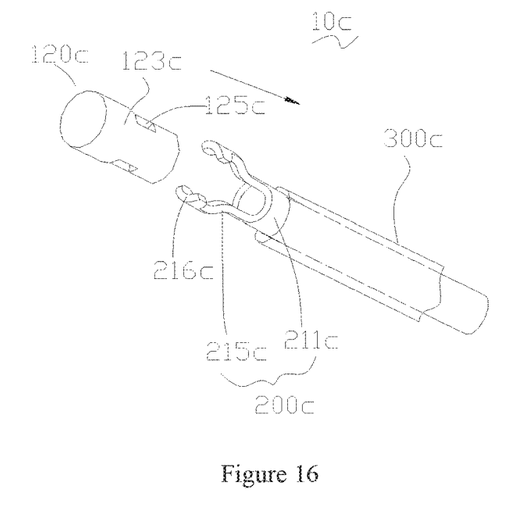
FIG. 16 is an exploded schematic diagram of an interventional medical system provided by another embodiment of the present disclosure.
Figure 17:
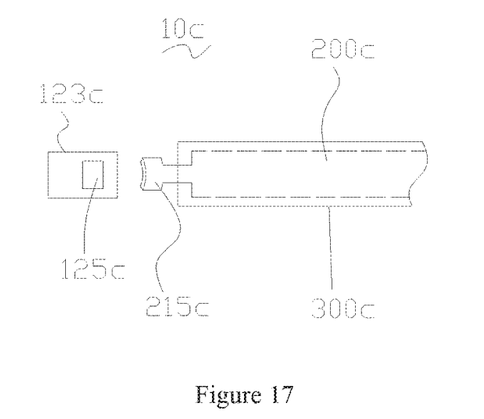
FIG. 17 is a side view of the interventional medical system in FIG. 16.
Figure 18:
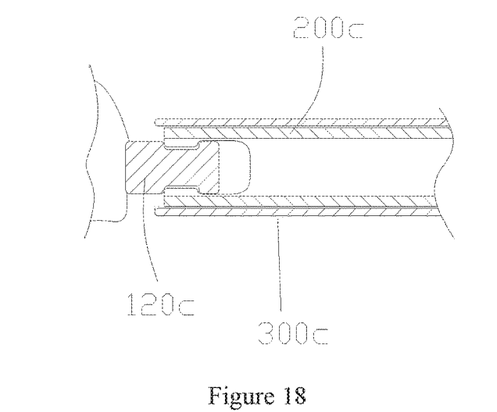
FIG. 18 is a combination schematic diagram of the interventional medical system in FIG. 16.

With reference to FIGS. 16, 17 and 18, an interventional medical system 10c provided by another embodiment of the present disclosure is approximately the same as the interventional medical system 10b, and includes an interventional medical device having a plug head portion 120c, a delivery cable 200c, and a locking sleeve 300c which surrounds the delivery cable 200c and may move relative to an axial direction of the delivery cable 200c.

The plug head portion 120c is approximately the same as the plug head portion 120b, but the difference is that the plug head portion 120c includes a solid connection section 123c, and first locking slots 125c are formed in the side wall of the connection section 123c. It can be understood that in other embodiments the connection section 123c also may be of a hollow structure, and at the moment, the first locking slots 125c may be separated from a tubular cavity of the connection section 123c; in other words, the first locking slots 125c do not penetrate through the inner wall of the connection section 123c.

The delivery cable 200c is approximately the same as the delivery cable 200b, and includes second locking pieces 215c which extend approximately away from the central axial line of a cable head portion 211c and has uniform thicknesses. But the difference is that the distal end sections 216c of the second locking pieces 215c are slightly closer to the central axial line of the cable head portion 211c than their adjacent sections, so that the distal end sections 216c of the second locking pieces 215c may better enter the first locking slots 125c to achieve the connection between the plug head portion 120c and the delivery cable 200c.

The locking sleeve 300c is approximately the same as the locking sleeve 300b, but the difference is that the thickness and the size of the locking sleeve 300c may be different from those of the locking sleeve 300b according to clinical requirements, and no additional details will be described here.

When the locking sleeve 300c radially restrains the second locking pieces 215c of the delivery cable 200c to the side wall of the connection section 123c of the plug head portion 120c (namely when the second locking pieces 215c form a limiting slot for containing the connection section 123c in an encircling manner under radial restriction applied by the locking sleeve 300c), the distal end sections 216c of the second locking pieces 215c are locked into the first locking slots 125c to achieve the connection between the delivery cable 200c and the interventional medical device having the plug head portion 120c.

It can be understood that in other embodiments, there may be one second locking piece 215c or one first locking slot 125c as long as the second locking pieces 215 may abut the wall of the connection section 123c to connect the interventional medical device 110c with the delivery cable 200c under the radial restriction applied by the locking sleeve 300c. It also can be understood that in other embodiments, under the radial restriction applied by the locking sleeve 300c, each first locking slot 125c may also contain two or more second locking pieces 215c as long as the interventional medical device 110c is connected with the delivery cable 200c. For example, two or more second locking pieces 215c abut the slot wall of one first locking slot 125c or are clamped in one first locking slot 125c.

Figure 19:
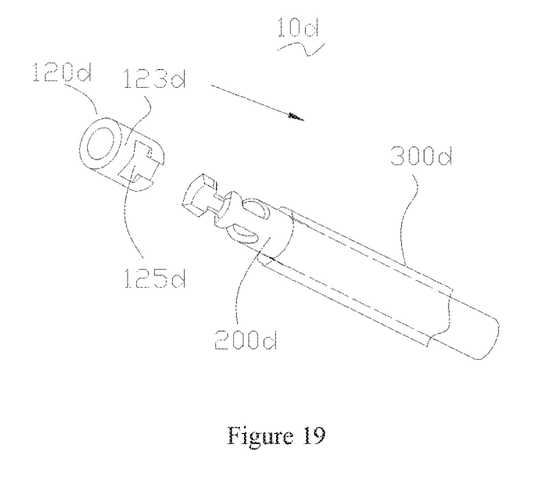
FIG. 19 is an exploded schematic diagram of an interventional medical system provided by another embodiment of the present disclosure.
Figure 20:
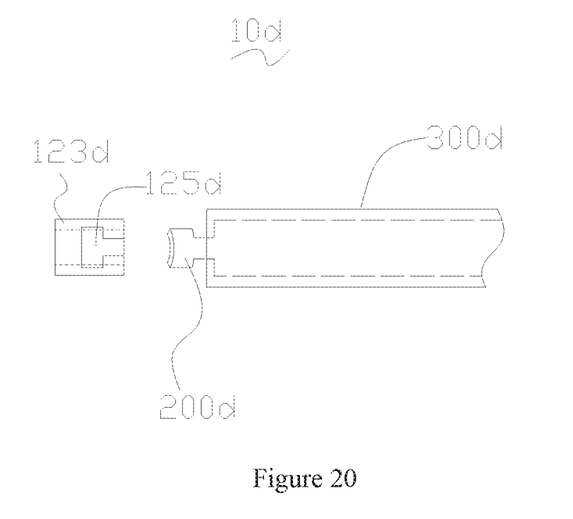
FIG. 20 is a side view of the interventional medical system in FIG. 19.

With reference to FIG. 19 and FIG. 20, an interventional medical system 10d provided by another embodiment of the present disclosure includes an interventional medical device having a plug head portion 120d, a delivery cable 200d, and a locking sleeve 300d which surrounds the delivery cable 200d and may move relative to an axial direction of the delivery cable 200d.

Figure 21:
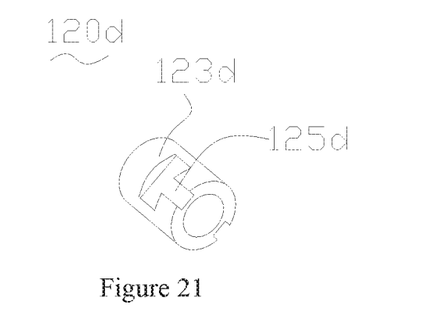
FIG. 21 is a schematic diagram of a plug head portion of the interventional medical device of the interventional medical system in FIG. 19.

The plug head portion 120d is approximately the same as the plug head portion 120b, and includes a hollow connection section 123d. But the difference is that T-shaped first locking slots 125d are formed in the side wall of the connection section 123d, and are separated from the tubular cavity of the connection section 123d, and the proximal ends of the first locking slots 125d penetrate through the proximal end surface of the connection section 123d. It can be understood that in other embodiments, the connection section 123d also may be of a solid structure. It can be understood that the first locking slots 125d may also be L-shaped locking slots, C-shaped locking slots or locking slots in other shapes, and not limited to the T-shaped locking slots in this embodiment.

The delivery cable 200d is approximately the same as the delivery cable 200, but the difference is that the thicknesses and the sizes of all elements of the delivery cable 200d may be different from those of all corresponding elements of the delivery cable 200 according to clinical requirements as long as the thicknesses of the locking pieces of the delivery cable 200d are uniform, and no additional details will be described here.

The locking sleeve 300d is approximately the same as the locking sleeve 300, but the difference is that the thickness and the size of the locking sleeve 300d may be different from those of the locking sleeve 300 according to the clinical requirements, and no additional details will be described here.

When the locking sleeve 300d radially restrains the second locking pieces 215d of the delivery cable 200d to the side wall of the connection section 123d of the plug head portion 120d (namely when the second locking pieces 215d form a limiting slot for containing the connection section 123d in an encircling manner under radial restriction applied by the locking sleeve 300d), the second locking pieces 215d are at least partially locked into the first locking slots 125d to achieve the connection between the delivery cable 200d and the interventional medical device.

It can be understood that in other embodiments, there also may be one second locking piece 215d or one first locking slot 125d as long as the second locking pieces 215d may abut the connection section 123d to connect the interventional medical device with the delivery cable 200d under the radial restriction applied by the locking sleeve 300d. It also can be understood that in other embodiments, under the radial restriction applied by the locking sleeve 300d, each first locking slot 125d also may contain two or more second locking pieces 215d as long as the interventional medical device is connected with the delivery cable 200d, for example, two or more second locking pieces 215d abut the slot wall of one first locking slot 125d or are clamped in one first locking slot 125d.

All technical features of the above-mentioned embodiments may be randomly combined. To make their descriptions simple, not all possible combinations of all the technical features in the above-mentioned embodiments are described, but the combinations of these technical features shall all be deemed as the scope of this description in case of no contradictions.

The above-mentioned embodiments are only expressive of several implementation modes of the present disclosure, and their descriptions are relatively specific and detailed, but may not be understood as limitations to the scope of the patent for invention. It should be noted that ordinary persons skilled in the art can further make a plurality of deformations and improvements that all fall within the scope of protection of the present disclosure without departing from the concept of the present disclosure. Therefore, the scope of protection of the patent for invention shall be based on attached claims.

The invention claimed is:

1. An interventional medical system, comprising a device provided with a plug head portion and comprising a delivery cable provided with a cable head portion, wherein the interventional medical system further comprises:
   a locking sleeve movably surrounding an outside of the delivery cable, the locking sleeve having a proximal end and a distal end with an end surface;
   the plug head portion has a circumferential direction and comprises a proximal end surface and at least one locking slot which extends through the proximal end surface;
   the cable head portion has a central axis line and comprises at least one elastic locking piece which extends away from the central axis line;
   wherein under radial restriction applied by the locking sleeve, the at least one elastic locking piece of the cable head portion is contained in a separate one of the at least one locking slot of the plug head portion such that the plug head portion is connected with the cable head portion, and when the locking sleeve moves relative to the delivery cable to a position where the at least one elastic locking piece of the cable head portion is no longer radially restrained, the at least one elastic locking piece of the cable head portion elastically moves away from the at least one locking slot of the plug head portion such that the device is separated from the delivery cable;
   wherein the plug head portion comprises multiple mutually separated locking pieces; each of the at least one locking slot of the plug head portion is positioned between two adjacent mutually separated locking pieces of the multiple mutually separated locking pieces; and under radial restriction applied by the locking sleeve, each of the at least one elastic locking piece of the cable head portion is contained in one of the at least one locking slot of the plug head portion such that the plug head portion is connected with the cable head portion;
   wherein the plug head portion comprises a hollow main body section having an outer diameter; and
   wherein each of the mutually separated locking pieces has a curved outer surface, and wherein all of the mutually separated locking pieces form an outer diameter that is greater than the outer diameter of the hollow main body section; part of the end surface of the distal end of the locking sleeve is sunken towards the proximal end of the locking sleeve to form at least one containing groove; and when the locking sleeve radially restrains the at least one elastic locking piece of the cable head portion, the multiple mutually separated locking pieces of the plug head portion are at least partially contained in the at least one containing groove.

2. The interventional medical system of claim 1, wherein each of the at least one locking slot has a distal end and a proximal end, each of the distal end and the proximal end of each of the at least one locking slot has a length, wherein the length of the proximal end of each of the at least one locking slot of the plug head portion in the circumferential direction of the plug head portion is less than that of the distal end of each of the at least one locking slot of the plug head portion in the circumferential direction of the plug head portion.

3. The interventional medical system of claim 2, wherein each of the at least one locking slot of the plug head portion comprises a T-shaped structure.

4. The interventional medical system of claim 1, further comprising a limiting part contained in the delivery cable; and when the plug head portion is connected with the cable head portion, the at least one elastic locking piece of the cable head portion are also clamped between the limiting part and the locking sleeve.

5. The interventional medical system of claim 4, wherein the delivery cable comprises a hollow cable section having a distal end and a wall thickness; the at least one elastic locking piece of the cable head portion are arranged at the distal end of the hollow cable section; and a unilateral gap between the delivery cable and the limiting part is less than the wall thickness of the hollow cable section.

6. The interventional medical system of claim 1, wherein the hollow main body section and the mutually separated locking pieces of the plug head portion are of an integrated structure formed by cutting one hollow tube.

7. An interventional medical system, comprising a device provided with a plug head portion and comprising a delivery cable provided with a cable head portion, wherein the interventional medical system further comprises:
   a locking sleeve movably surrounding an outside of the delivery cable, the locking sleeve having a proximal end and a distal end with an end surface;
   the plug head portion has a circumferential direction and comprises a proximal end surface and at least one locking slot which extends through the proximal end surface;
   the cable head portion has a central axis line and comprises at least one elastic locking piece which extends away from the central axis line;
   wherein under radial restriction applied by the locking sleeve, the at least one elastic locking piece of the cable head portion is contained in a separate one of the at least one locking slot of the plug head portion such that the plug head portion is connected with the cable head portion, and when the locking sleeve moves relative to the delivery cable to a position where the at least one elastic locking piece of the cable head portion is no longer radially restrained, the at least one elastic locking piece of the cable head portion elastically moves away from the at least one locking slot of the plug head portion such that the device is separated from the delivery cable;
   wherein the plug head portion comprises multiple mutually separated locking pieces; each of the at least one locking slot of the plug head portion is positioned between two adjacent mutually separated locking pieces of the multiple mutually separated locking pieces; and under radial restriction applied by the locking sleeve, each of the at least one elastic locking piece of the cable head portion is contained in one of the at least one locking slot of the plug head portion such that the plug head portion is connected with the cable head portion;
   wherein each of the at least one locking slot has a proximal end and a distal end, each of the mutually separated locking pieces has a proximal end and a distal end, with the distal ends and the proximal ends of each of the at least one locking slot and each of the mutually separated locking pieces having a length, wherein the length of the proximal end of each of the at least one locking slot of the plug head portion in the circumferential direction of the plug head portion is less than the length of the distal end of each of the at least one locking slot of the plug head portion in the circumferential direction of the plug head portion, and the length of the proximal end of each of the mutually separated locking pieces of the plug head portion along the circumferential direction of the plug head portion is greater than the length of the distal end of each of the mutually separated locking pieces of the plug head portion along the circumferential direction of the plug head portion;

wherein the plug head portion comprises a hollow main body section having an outer diameter, and each of the mutually separated locking pieces of the plug head portion is arranged on the proximal end surface of the plug head portion; and wherein each of the mutually separated locking pieces has a curved outer surface, and wherein all of the mutually separated locking pieces form an outer diameter that is greater than the outer diameter of the hollow main body section; part of the end surface of the distal end of the locking sleeve is sunken towards the proximal end of the locking sleeve to form at least one containing groove; and when the locking sleeve radially restrains the at least one elastic locking piece of the cable head portion, the multiple mutually separated locking pieces of the plug head portion are at least partially contained in the at least one containing groove.

\* \* \* \* \*